(12) United States Patent
Hager et al.

(10) Patent No.: US 6,473,173 B1
(45) Date of Patent: Oct. 29, 2002

(54) METHOD FOR DETERMINING THE CONTENT OF PREDETERMINED INGREDIENTS WITH STOCHASTIC DISTRIBUTION IN GOODS WHICH ARE OF A SOLID AND NONHOMOGENEOUS CONSISTENCY

(75) Inventors: Jürgen Hager, Hückeswagen (DE); Walter Vieth, Wermelskirchen (DE); Dino Vieth, Wermelskirchen (DE)

(73) Assignee: Maqurit Gefrierschneider GmbH, Remscheid (DE)

( * ) Notice: Subject to any disclaimer, the term of this patent is extended or adjusted under 35 U.S.C. 154(b) by 0 days.

(21) Appl. No.: 09/485,356

(22) PCT Filed: Jun. 7, 1999

(86) PCT No.: PCT/DE99/01651

§ 371 (c)(1),
(2), (4) Date: Feb. 4, 2000

(87) PCT Pub. No.: WO99/64843

PCT Pub. Date: Dec. 16, 1999

(30) Foreign Application Priority Data

Jun. 5, 1998 (DE) .......................................... 198 25 095

(51) Int. Cl.⁷ ............................ G01N 21/31; B26D 7/27
(52) U.S. Cl. ...................................... 356/300; 356/326
(58) Field of Search ................................ 356/300, 319, 356/326, 328

(56) References Cited

FOREIGN PATENT DOCUMENTS

| DE | 3601443 | 7/1987 |
|----|---------|--------|
| EP | 0402877 | 12/1990 |
| GB | 15076834 | 4/1978 |
| JP | 4286938 | 12/1992 |
| JP | 9119894 | 6/1997 |

*Primary Examiner*—F. L. Evans
(74) *Attorney, Agent, or Firm*—Pandiscio & Pandiscio; Scott R. Foster

(57) ABSTRACT

The invention relates to a method for determining the content of predetermined ingredients in products (3) of solid and nonhomogeneous consistency, preferably foodstuffs, in which a measuring head is guided with its front face over an outer surface of the product in a sliding manner while in continuous and direct contact with the surface.

13 Claims, 4 Drawing Sheets

Figure 1:
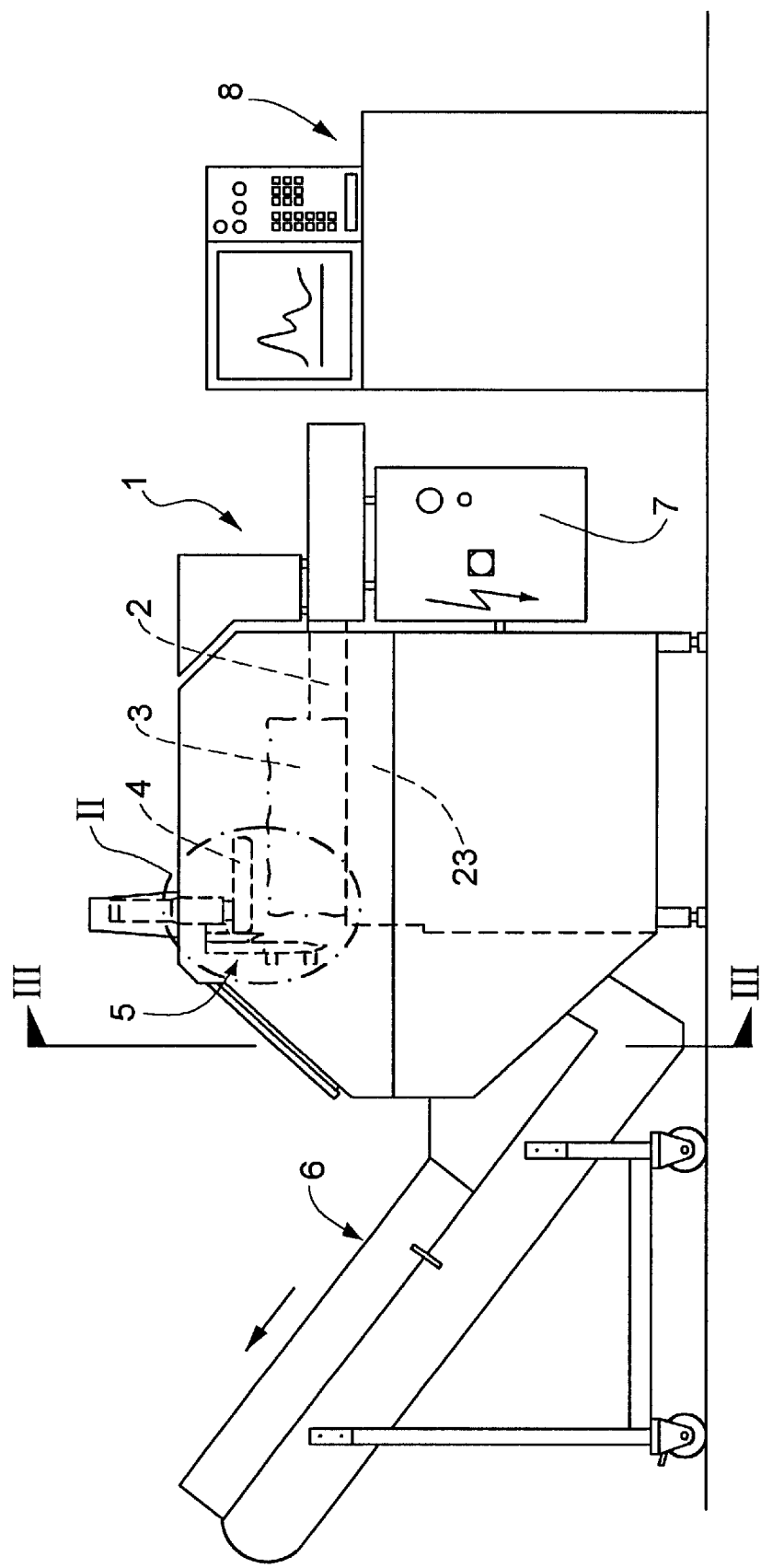

METHOD FOR DETERMINING THE CONTENT OF PREDETERMINED INGREDIENTS WITH STOCHASTIC DISTRIBUTION IN GOODS WHICH ARE OF A SOLID AND NONHOMOGENEOUS CONSISTENCY

The following invention relates to a method for determining the content of predetermined ingredients in sliceable products of solid and nonhomogenous consistency, such as foodstuffs, as well as a device for executing the method.

A special measuring method of this type for identifying surface defects in flat objects is known from DE OS 36 01 443. To do so, the transmitted light is captured and metrologically evaluated. The indirect surface contact between the measuring head and the product eliminates the problem of soilage.

A different special measuring method is based on the principle in which monochrome light is beamed into the surface of the merchandise item to be examined. The wavelength of the light is syntonized in a manner that certain molecules of the constituent substances to be determined are excited so that they vibrate. The light that is reflected back is transmitted into the light guide system by the measuring head. The reflected light is then processed via an optical grid in such a way that it can be spectrometrically analyzed.

The light so analyzed provides information about the prevailing content of the ingredient in the product sample that is to be examined.

Since a constant relative motion occurs between the product and the measuring head, stochastically distributed components can also be examined in the product.

The relative motion between the product and the measuring head causes a path-integral measurement to take place at the surface of the product sample, which can then be converted to a volume integral by means of statistical methods.

This principle can be applied in many ways. It is especially suited to monitoring processes in industrial manufacturing, including the sustained monitoring of material compounds, such as bulk materials or liquids.

In addition, the known method allows for both contactless and contact-bound readings.

The contactless measuring method, however, requires that the measuring head which represents the end of the light guide system, remain unobstructedly transparent to light during the entire process.

This cannot be ensured in all methods.

Therefore, the problem that the measuring head may become soiled must be taken into consideration when selecting the measuring method in each particular case.

Alternatively, there is the contact-bound measuring method, such as it is applied in guide rollers for product trains. Here, various measuring heads are distributed over the sleeve of the guide roller to perform the measurements as they come into temporary contact with the outside of the product train as it passes through.

Both measuring methods, however, have disadvantages with regard to certain product types.

For instance, no measuring method is well suited for products of a slightly greasy consistency because of the problem of soil accumulation (=dulling) on the measuring head, which occurs both in the contactless and the contact-bound method.

An important example of an application of this known method is the monitoring of meat processing operations. For products of this kind, the object is to be able to determine a specific level of components within the most narrow tolerances possible, or to obtain it by means of admixing. In sausage production it is for instance necessary to know the fat content of the ground meat beforehand. The stochastic distribution of the fatty materials in the meat is crucial in this instance because the fat is not homogeneously mixed with the meat. This creates the problem of being able to predict the expected result even in the pre-grinding stage.

The aspect of predicting the end result is thus of the greatest importance. To do so, the result must be predictable within a very narrow tolerance. If it is found during the processing of a specific batch that the desired goal cannot be achieved, an adjustment must be made by technical means in order to produce a total batch having the desired content of the respective components, by admixing certain predetermined amounts of ground material from other batches.

It must be expressly noted here that a partial aspect of the invention also consists in the ability to measure different components, such as protein, collagen, water, salts, etc., and to express them in percentages by weight, for example.

Thus, the objective of the invention is to refine the contact-bound measuring method for products that are subject to a process of size reduction so that, with a minimum amount of equipment, it can be applied to the type of product where the dulling of the measuring head has so far been unavoidable.

The invention offers the advantage that the constant surface contact between the measuring head and a surface of the product to be examined prevents the measuring head from becoming dulled.

This advantage is accomplished in that only the complete front face of the measuring head is kept in surface contact with the product while a constant relative movement to the product is maintained.

This keeps greasy particulates which adhere to the surface of the product from settling on the measuring head. As a result of the relative movement between the measuring head and the surface of the product, the entire front face is constantly being wiped clean.

The constant contact during the relative movement creates a cleaning-off effect on the measuring head and ensures a highly accurate and precise measurement.

Another essential feature is the predetermined contact pressure between the measuring head and the product which ensures the wiping effect to keep the front face of the measuring head free of the greasy deposits which would otherwise settle on it.

The constant sliding motion between the front face of the measuring head and the outer surface of the product prevents any undesirable interference during the measuring cycle. The sliding motion, so to speak, automatically ensures that the light intake surface at the front face of the measuring head is kept clean. The self-cleaning effect is thus essential to the invention.

The light from the light guide system can thus enter the product unimpeded, and the light reflected from it can return into the light guide.

It must be expressly noted that the method described in this invention can also be applied for products whose surface consistency is not greasy.

However, due to the self-cleaning effect, the method is particularly suited for product samples of meat-like consistency. Especially in the area of industrial sausage manufacture involving the preliminary size reduction of meat in chunks, the method offers significant advantages. This will be addressed later.

The measuring head rotates either in an oscillating or a unidirectional fashion. This is a refinement that is suited to the lot-by-lot processing of large product batches.

In addition, oscillating measuring heads can be made to execute one empty sweep after each measuring sweep.

This measure is designed to obtain a uniform wiping direction at the front face of the measuring head. The measuring head is thus always swept clean in the same direction. In the opposite direction, no contact between the front face of the measuring head and the product can occur.

Particularly when shredding meat, and preferably frozen meat, the process is very easily integrated into the size reduction process.

It is provided to this effect that the movement of the measuring head be coupled to the movement of the cutting device. Since a measurement is performed simultaneously with each cutting movement at the cutting surface or a surface that is parallel thereto, the result thus is a two-dimensional measuring protocol over the length of the product with each one-dimensional movement of the measuring head.

In addition, several measuring heads can be arranged parallel to each other to produce a three-dimensional network of readings.

The method is particularly suited to fully automated data processing. In this application, the data obtained during the continuous measuring process is evaluated at predetermined intervals.

Since during the continuous measuring process the measuring signal is generated continuously but is constantly changing, the intervals at which the readings are evaluated should be more than 20 milliseconds apart. Since the measuring speed lies at about 20 centimeters per second, a more than sufficiently precise measuring protocol can be expected along the measuring path. A single measurement must be established as a lower limit for each cutting level.

In addition, there should be a capability for performing calibrations in order to allow for the use of the same method for a great variety of products. This also provides the advantage of adjusting worn measuring components, for example.

The method is especially useful when coupled with an admixing procedure.

The objective of an admixing procedure is to obtain an artificial product mix for which the percentage of the ingredient in question is specified.

To do so, the precise percentage of the ingredient in question in each lot within the total batch must be determined. By means of the appropriate numerical integration across the entire volume of the batch it is then possible to predict what percentage of the ingredient will be present.

Any deviation from the desired value can then be corrected by the timely admixture of lots which have a different content.

The invention thus offers the advantage that the great fluctuation ranges that are customary nowadays, such as for example the fat content listed for salami, can be significantly reduced.

The achievable range of fluctuation is expected be significantly less than ±1%.

A significant feature in this device is the flush, seamless border shared by the measuring head and the surface of the measuring head bracket which faces the product. Nothing can accumulate on this smooth and continuous surface.

On the one hand, the constant contact with the product by the measuring head reduces the wear and tear of the measuring head to a minimum, while on the other hand the measuring head itself is continuously wiped clean. No clogging of border seams, etc. will occur.

Advantageous refinements are derived from the subclaims.

Figure 2:
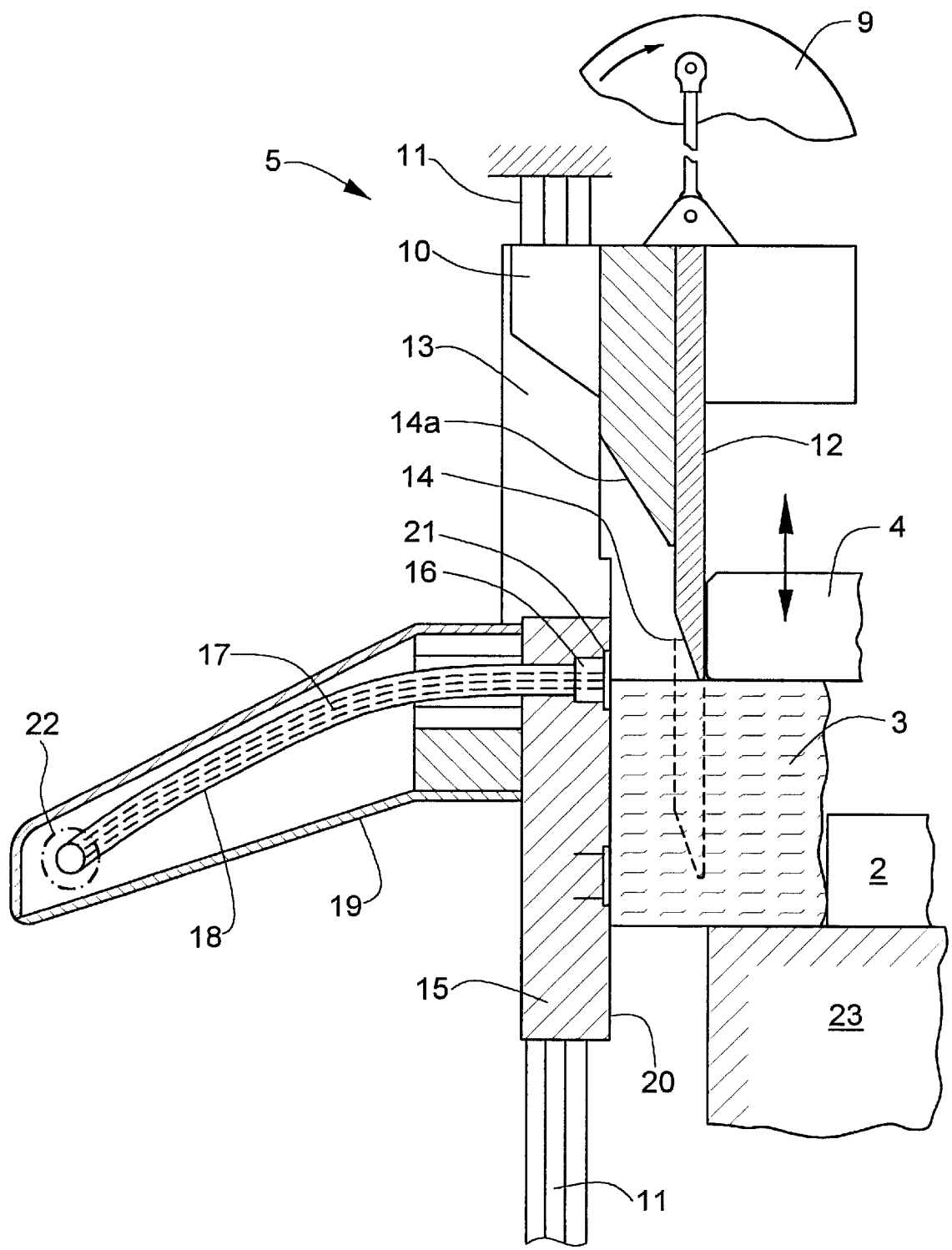
Figure 3:
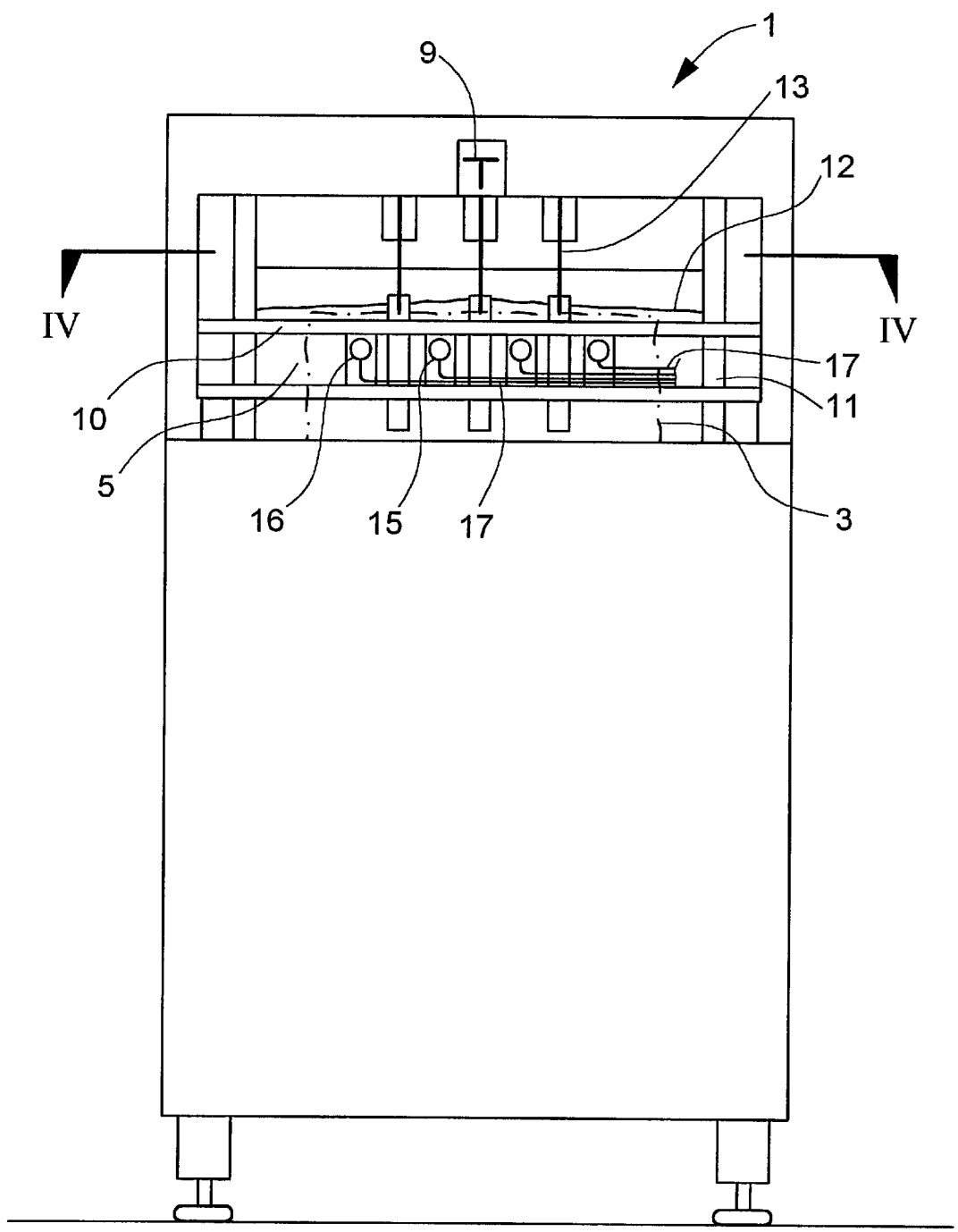
Figure 4:
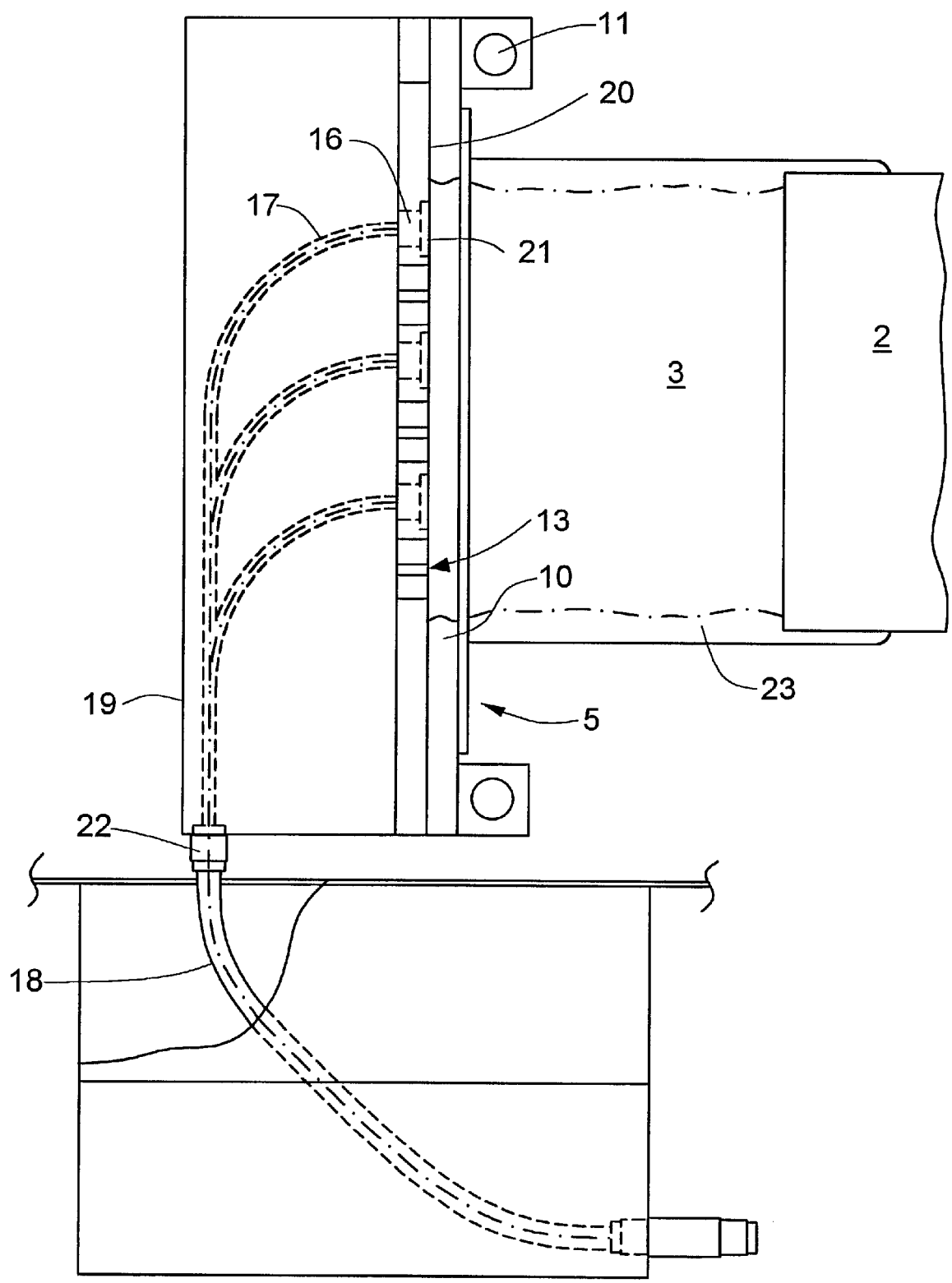

In the following, the invention will be explained in greater detail by means of various embodiments. Shown are:

FIG. 1, an embodiment of the invention in a size reduction machine for frozen meat;

FIG. 2, a detailed view of Area II, according to FIG. 1;

FIG. 3, a view according to Line III—III from FIG. 1;

FIG. 4, a cutting unit seen from above along Line IV—IV from FIG. 3.

The figures show a size reduction machine 1, as customarily used and known for shredding frozen meat 3. The frozen meat 3 rests on the machine body 23 and is incrementally moved along on a conveyor table 2. In front of the top surface of the frozen meat 3, in the conveying direction, there is a cutting unit 5. To cut the block of frozen meat 3 into small pieces, there is a holding die 4 which holds the frozen meat 3 from above for as long as the cutting unit 5 is active.

The cutting unit 5 cuts slice-like pieces off the frozen meat 3, after which the slices are cut into vertical strips. These small meat pieces drop onto the endless loop conveyor 6, from where they travel to the next processing stage.

All of the necessary electrical and other controls are housed inside the control panel 7. The size reduction machine 1 is equipped with a central processing unit 8 which plays an important role in this process. This area will be addressed later. The cutting unit 5, which moves in an oscillating fashion, is driven in a vertical direction. Additional details hereto are shown in FIG. 2. By way of example and without limiting the invention to this design, it shows the oscillating drive 9 as a crank and connecting rod connection which moves the cutting unit 5 vertically up and down in its longitudinal guide 11. Other oscillating drives, such as piston-cylinder units (see FIG. 3), linear motors, spindle drives, etc. can also be used.

The oscillating drive 9 acts on the cutting sled 10 which carries all of the required individual knives and the measuring head bracket 15.

These knives are comprised of the principal knife 12 and several cross knives 13 arranged downstream. As the principal knife 12 cuts top-side slices off the block of frozen meat 3, the slices are cut into vertical strips by the cross knives 13 which follow next.

To this effect, it is necessary for the top slice of the frozen meat 3, as it is being separated, to be forced through the cross knives 13 which are arranged in the form of a grid.

This is accomplished first by means of the slanted edge of the principal knife 14 which includes an acute angle with the cutting surface at the frozen meat 3. The leading edge of the principal knife slant 14 forces the top slice that has just been cut off in the direction of the measuring head bracket 15, where the top slice is held fast.

As the principal knife 12 plunges in deeper, the slant rack 14a enters the groove just opened by the principal knife 12.

This causes the top slice to be forced in the direction of the grids of the cross knives 13, where it is inevitably separated into vertical strips.

Firmly joined to the measuring head bracket 15 is a measuring head 16 whose front face lies flush against the surface of the measuring head bracket 15 which faces toward the frozen meat 3.

As a result, the front plane 20 slips off the surface of the top slice which faces toward the front, while the cutting sled 10 plunges into the frozen meat 3.

During this process, the front surface of the top slice always lies flush against the front plane 20 of the measuring head bracket 15, causing the front face of the measuring head 16 to slide across the outer surface of the product.

During this movement, the slanted edge of the principal knife 14, in conjunction with the slant rack 14a, ensures that a predetermined contact pressure is exerted between the front plane 20 and the top slice, while the cutting sled 10 is simultaneously imprinted, by means of the oscillating drive 9, with a predetermined relative speed with respect to the frozen meat 3.

Because the front face of the measuring head 16 is in constant contact with the frozen meat 3, it wipes itself continuously clean automatically, so to speak. The deposit of grease, water or the like is thus reliably prevented, allowing the measuring head 16 to do its job unimpeded.

This job consists in allowing a light beam, conducted to the front face of the top slice via the light wave guide 17, to beam into this front face in as unimpeded a fashion as possible. Since this light is monochromatic, certain atoms and molecules in front of the front face of the measuring head are excited so as to vibrate in a certain way. These in turn imprint a certain wave length spectrum on the reflected light which can then be spectrometrically analyzed and evaluated.

It is thus essential for the front face of the measuring head to be kept completely transparent to light even when processing products of this type from the food industry.

This is ensured by the continuous frictional movement between the front face of the measuring head and the product.

Once the cut described above has been completed, the cutting sled 10 rises again until the conveyor table 2 can move the block of frozen meat 3 another incremental step in the direction of the measuring head bracket 15.

The cutting surface that was just created once again lies flush against the measuring head 16 and the process is repeated.

The measuring head 16 is directly coupled to the oscillating movement of the cutting sled 10 by means of the measuring head bracket 15 and moves along a vertical linear path. Its readings thus represent a line integral which extends over the height of the block of frozen meat 3.

Because the measuring head 16 is constantly flush against the front surface of the block of frozen meat 3, the measuring signal is read as an analog value.

In order to limit the resulting overabundance of data, which is entirely permissible given the desired accuracy which allows for a deviation of approximately 1%, it is further provided that the readings be evaluated only at certain predetermined intervals.

These intervals should be at least 20 milliseconds apart.

After the knife assembly 5 has cut a top slice off the block of frozen meat 3, the cutting sled 10 rises in an empty trip.

In so doing, the front area of the measuring head passes freely by the block of frozen meat 3. The conveyor table 2 then advances the frozen meat by the thickness of another top slice until the cut surface that has just been produced lies flush against the measuring head bracket 15.

Since the movement of the measuring head 16 in the present case is also coupled with that of the knife assembly which serves to cut the frozen meat 3 into small pieces, there is a direct relationship between the precision of this method and the thickness of the top slice that is cut off the frozen meat 3.

This represents a particular advantage of the invention, inasmuch as the accuracy of the determination of the fat content in the frozen meat thus is a function of the thickness of the various top slice cuts. Moreover, already installed size reduction machines of this type can be retrofitted to accommodate this process without impairing their accuracy.

Furthermore, the readings that were obtained and evaluated can easily be stored by adding a processing unit 8. The percentage of fat by volume contained in the frozen meat can thus be calculated based on the amount of frozen meat processed and by summing up the line integral values emitted by the measuring head 16 during its back-and-forth sweeps.

In rounding out the above, FIGS. 3 and 4 show several parallel measuring heads 16 next to each other which move across the product at the same time and over the same distance.

Based on the readings obtained from one sweep, a surface-integral mean value can be calculated, the sum of all of which, over the total length of the block of frozen meat 3, yields a reliable volume integral.

To adapt this measuring method to a variety of products, the design can provide for a circuit to allow for the calibration of the readings. Such a circuit is easy to integrate into the processing unit 8.

Of particular advantage in this invention is the fact that it can be coupled with an admixing process in such a way that, for example, it allows the fat content of a whole batch of frozen meat to be determined. By admixing additional amounts of frozen meat, fatty frozen meat or fat, it is thus possible to preset a specific desired fat content for the entire batch.

To be able to do this, however, the fat content of the batch being processed must be determined with sufficient accuracy.

The invention allows readings to be made with an accuracy of +1% or better. It should be added that the measuring head 16 is shielded from the product 3 by means of a glass pane 21. The contour of the glass pane is seated firmly and virtually without any gap in an appropriately sized recess at the measuring head bracket 15.

To the rear of the measuring head 16, a connection has been provided for a light wave guide 17 which extends within a protective tube 18. The protective tube 18 leads to a connecting adapter 22, from where the light wave guides 17 of several measuring heads are wired to the processing unit 8.

In rounding out the above, the illustration also shows that the protective tube 18 is accommodated inside a housing 19 which is joined to the measuring head bracket 15 at the surface that faces away from the product 3.

This housing 19 provides added protection against mechanical damage for the light wave guides 17 which extend inside the protective tubes 18. The housing 19 is slightly slanted toward its lower end, so that any meat pieces which may fall on it are passed on to the endless loop conveyor 6.

The measuring head brackets 15 are comprised of narrow profile rods. In conjunction with the specified contact pressure of the conveyor table 2, the narrow support surface ensures a high contact pressure and results in an efficient self-cleaning effect.

What is claimed is:

1. A method for determining content of predetermined ingredients with stochastic distribution in a sliceable food products (3) of solid and nonhomogeneous consistency, during incremental size reduction of said product by means of a knife assembly, in which a light beam emanating from a measuring head (16) of a light guide system (17, 8) is beamed into the product (3), and the light reflected from the product (3) and into the measuring head (16) is spectrometrically analyzed and evaluated, and in which the measuring head (16), which is coupled to the movement of the knife assembly, is guided, with its front face and in a sliding fashion, over an outer surface of the product under direct surface contact, under a predetermined contact pressure, and at a predetermined relative speed.

2. The method according to claim 1, wherein the incremental size reduction occurs in slices, and wherein every time a slice is cut, the product is advanced until the cut surface just generated lies flush against the measuring head (16).

3. The method according to claim 1 wherein the movement of the measuring head (16) is an oscillating movement (9) and takes place preferably in a linear path.

4. The method according to claim 3, wherein each measuring movement is followed by a non-measuring movement.

5. The method according to claim 1 wherein the movement of the measuring head is executed unidirectionally in one rotational path.

6. The method according to claim 1 wherein several measuring heads (16) travel across the product next to and parallel to each other at the same time and over the same distance.

7. The method according to claim 2, wherein measurements during surface contact are recorded continually and wherein their evaluation takes place only in specific intervals.

8. The method according to claim 7, wherein the intervals for evaluating the measurements are more than 20 milliseconds apart.

9. The method according to claim 8, characterized in that the measurements are calibrated.

10. The method according to claim 1, wherein the measuring method is coupled with an admixing procedure, in which all of the product (3) of a complete batch is processed lot-by-lot in such a way that, for each lot, the actual content value for an ingredient in question is determined separately, and wherein an integral value of the complete batch is adjusted so as to have a specific predetermined integral value by admixing lots whose content has been appropriately adjusted.

11. Device for determining content of a sliceable food product, said device comprising a take-up device (2, 4) for the product (3) and a measuring head bracket (15) joined to a measuring head (16) and movable relative to the product (3) and coupled to a cutting assembly, and in which a front area of the measuring head (16) borders flush and seamless on a plane (20) of the measuring head bracket (15) which faces the product (3), and a pressure device (2, 14, 14a) which presses the product (3) against the movable measuring head bracket (15).

12. Device according to claim 11, wherein the measuring head (16) is shielded from the product (3) by a glass pane (21) that is seated in a recess of the measuring head bracket (15) which corresponds to the edge contours of the glass pane (21).

13. Device according to claim 11, wherein a light wave guide (17) emanates from the plane of the measuring head bracket facing away from the product (3) and is mechanically protected (18, 19) inside a housing (19) which surrounds it and is wired to a connecting adapter (22) that is permanently attached to the housing (19).

* * * * *